United States Patent
Abenaim et al.

(10) Patent No.: US 9,116,248 B2
(45) Date of Patent: Aug. 25, 2015

(54) DETECTOR ARRAY HAVING EFFECTIVE SIZE LARGER THAN ACTUAL SIZE

(75) Inventors: Daniel Abenaim, Lynnfield, MA (US); Steve Urchuk, Melrose, MA (US); Ram Naidu, Newton, MA (US); Ruvin Deych, Gloucester, MA (US)

(73) Assignee: Analogic Corporation, Peabody, MA (US)

( * ) Notice: Subject to any disclaimer, the term of this patent is extended or adjusted under 35 U.S.C. 154(b) by 68 days.

(21) Appl. No.: 14/000,363

(22) PCT Filed: Feb. 17, 2011

(86) PCT No.: PCT/US2011/025166
§ 371 (c)(1),
(2), (4) Date: Aug. 19, 2013

(87) PCT Pub. No.: WO2012/112153
PCT Pub. Date: Aug. 23, 2012

(65) Prior Publication Data
US 2013/0320222 A1    Dec. 5, 2013

(51) Int. Cl.
*G01T 1/20* (2006.01)
*G01T 1/16* (2006.01)
(Continued)

(52) U.S. Cl.
CPC . *G01T 1/16* (2013.01); *A61B 6/032* (2013.01); *A61B 6/4021* (2013.01); *G01T 1/2006* (2013.01); *G01T 1/2018* (2013.01);
(Continued)

(58) Field of Classification Search
CPC ....................................................... G01T 1/16
USPC ................................................ 250/366, 393, 394
See application file for complete search history.

(56) References Cited

U.S. PATENT DOCUMENTS 5,241,180 A * 8/1993 Ishaque et al. ............ 250/361 R
6,272,207 B1   8/2001 Tang
(Continued)

FOREIGN PATENT DOCUMENTS

CA   2754034 A1   7/2010
EP   1314976 A2   5/2003
(Continued)

OTHER PUBLICATIONS

Korean Office action dated Nov. 18, 2014, 15 pages.
(Continued)

*Primary Examiner* — David Porta
*Assistant Examiner* — Meenakshi Sahu
(74) *Attorney, Agent, or Firm* — Cooper Legal Group LLC

(57) ABSTRACT

One or more techniques and/or systems described herein provide for a detector array having an effective size that is larger than its actual size of its elements, thus reducing costs by reducing materials required. In one embodiment, one or more channels of the detector array are removed (e.g., and filled with a radiation absorbing material) to create what may be referred to as a sparse array. In another embodiment, one or more channels of a detector array comprise a detection portion and a dead space (e.g., filled with a radiation absorbing material). In yet another embodiment, one or more channels of a detector array comprise light focusing mechanisms configured to focus light from a scintillator portion of an indirect conversion detector array to a photodetector portion of the detector array, where a detection surface area of the photodetector is less than a detection surface area of the scintillator.

25 Claims, 6 Drawing Sheets

(51) Int. Cl.
*A61B 6/03* (2006.01)
*A61B 6/00* (2006.01)
*G01T 1/24* (2006.01)

(52) U.S. Cl.
CPC ............... *G01T 1/243* (2013.01); *G01T 1/244* (2013.01); *A61B 6/508* (2013.01)

(56) References Cited

U.S. PATENT DOCUMENTS

| | | |
|---|---|---|
| 2005/0072930 A1 | 4/2005 | Hoffman |
| 2005/0259790 A1* | 11/2005 | Gerndt et al. ............... 378/98.12 |
| 2007/0098138 A1* | 5/2007 | Bessho ............................ 378/19 |
| 2010/0096555 A1* | 4/2010 | Nelson ..................... 250/363.04 |
| 2012/0207370 A1* | 8/2012 | Fahimian et al. ............. 382/131 |

FOREIGN PATENT DOCUMENTS

| | | |
|---|---|---|
| JP | 2000098536 | 4/2000 |
| JP | 2001074847 | 3/2001 |
| JP | 2005009872 | 1/2005 |
| JP | 2005129558 | 5/2005 |
| JP | 2006059901 | 3/2006 |
| JP | 2007105068 | 4/2007 |
| JP | 2007125086 | 5/2007 |
| JP | 2007519461 A | 7/2007 |
| JP | 2012159483 | 8/2012 |
| WO | 02085079 A2 | 10/2002 |

OTHER PUBLICATIONS

International Search Report cited in related application No. PCT/US2011/25166 dated Feb. 17, 2011.

* cited by examiner

DETECTOR ARRAY HAVING EFFECTIVE SIZE LARGER THAN ACTUAL SIZE

BACKGROUND

The present application relates to a detector array of an x-ray imaging system (e.g., a radiography and/or CT system). It finds particular application with x-ray imaging systems that comprise large detector arrays (e.g., that may span 1 meter or more in length and/or ½ meter in width), but also applies to smaller detector arrays as well. Such detector arrays are commonly used in medical, security, and/or industrial x-ray imaging systems, for example.

X-ray imaging systems, such as projection radiography systems, computed tomography (CT) systems, line scanners, etc., provide information, or images, of the inside of an object under examination (e.g., interior aspects of an object under examination). That is, an object under examination by the x-ray imaging system is exposed to radiation, and one or more images are formed based upon the radiation absorbed by the object, or rather an amount of radiation that is able to pass through the object. Typically, highly dense objects absorb (e.g., attenuate) more radiation than less dense objects, and thus an object having a higher density, such as a bone or metal object, for example, will appear differently than less dense objects, such as fatty tissue or clothing, for example.

Traditionally x-ray images were formed using x-ray film. The film was exposed to radiation, or light yielded from the radiation (e.g., if intensifying screens were placed between the film and the radiation source), and a visible pattern of metallic black silver was produced on the film. The degree of blackening (e.g., the amount of metallic black silver produced) depended upon the intensity of the radiation (e.g., the magnitude of radiation absorbed by the object). Thus, the detector array was essentially comprised of an x-ray film and possibly one or more intensifying screens.

More recently, the x-ray film and the intensifying screens have been replaced with digital detector arrays (e.g., such as those commonly found in digital radiography and CT systems) that are configured to convert radiation, either directly or indirectly, into electric current that is measured to yield electrical signals. The amount of electric current measured is proportional to the number of radiation photons that impacted the digital detector array and can be used to create an image(s) of the object under examination.

It will be appreciated to those skilled in the art that there are two basic types of digital detector arrays, direct conversion detector arrays and indirect conversion detector arrays. Direct conversion detector arrays are typically configured to convert detected radiation directly into electric charge using a crystalline or amorphous material, for example. Indirect conversion detector arrays are generally configured to convert detected radiation into another medium, typically light, before the electric charge is produced. Thus, for example, indirect conversion detector arrays may convert radiation into light using a scintillator material (e.g., Cadmium Tungstate, Bismuth Germanate, Cesium Iodide, Sodium Iodide, etc.) and may subsequently convert the light into electric charge using a photodetector array (e.g., a plurality of photodiodes). Generally, in both direct and indirect conversion detector arrays, the electric charge is detected/measured using an electronic, pixelated array (e.g., a thin-film transistor (TFT) array comprising a two-dimensional (2D) capacitor array).

While digital detector arrays have proven effective for imaging (e.g., and have many benefits over x-ray film), the cost of manufacturing a digital detector array can cost several tens of thousands of dollars or more, depending upon its size, among other things. For large scale x-ray imaging systems that may comprise detector arrays measuring one meter by one-half a meter, for example, such as those comprised in baggage systems and/or systems commonly found in industrial applications, the cost of a detector array may be approximately 30% of the total system cost. Such cost may make implementation of an x-ray imaging system cost prohibitive in some applications.

SUMMARY

Aspects of the present application address the above matters, and others. According to one aspect an x-ray examination apparatus is provided. The x-ray examination apparatus comprises a detector array having an effective size that is greater than its actual size.

According to another aspect, an x-ray examination apparatus is provided. The x-ray examination apparatus comprises a detector array having an effective size that is greater than its actual size. The detector array comprises a plurality of channels and one or more dead spaces. The dead spaces being intentionally inserted into the detector array.

According to yet another aspect, an x-ray examination apparatus is provided. The x-ray examination apparatus comprises an indirect conversion detector array. The indirect conversion detector array comprises a scintillator material configured to convert radiation emitted from a radiation source into light and a photodetector configured to convert the light generated by the scintillator material into electric charge. The indirect conversion detector array also comprises one or more light focusing mechanisms configured to focus light generated by a scintillator material onto the photodetector.

According to another aspect, a method is provided. The method comprises correcting for a difference between an actual area of a detection surface of a detector array and an effective area of the detection surface of the detector array.

FIGURES

The application is illustrated by way of example and not limitation in the figures of the accompanying drawings, in which like references indicate similar elements and in which.

DESCRIPTION

Figure 1:
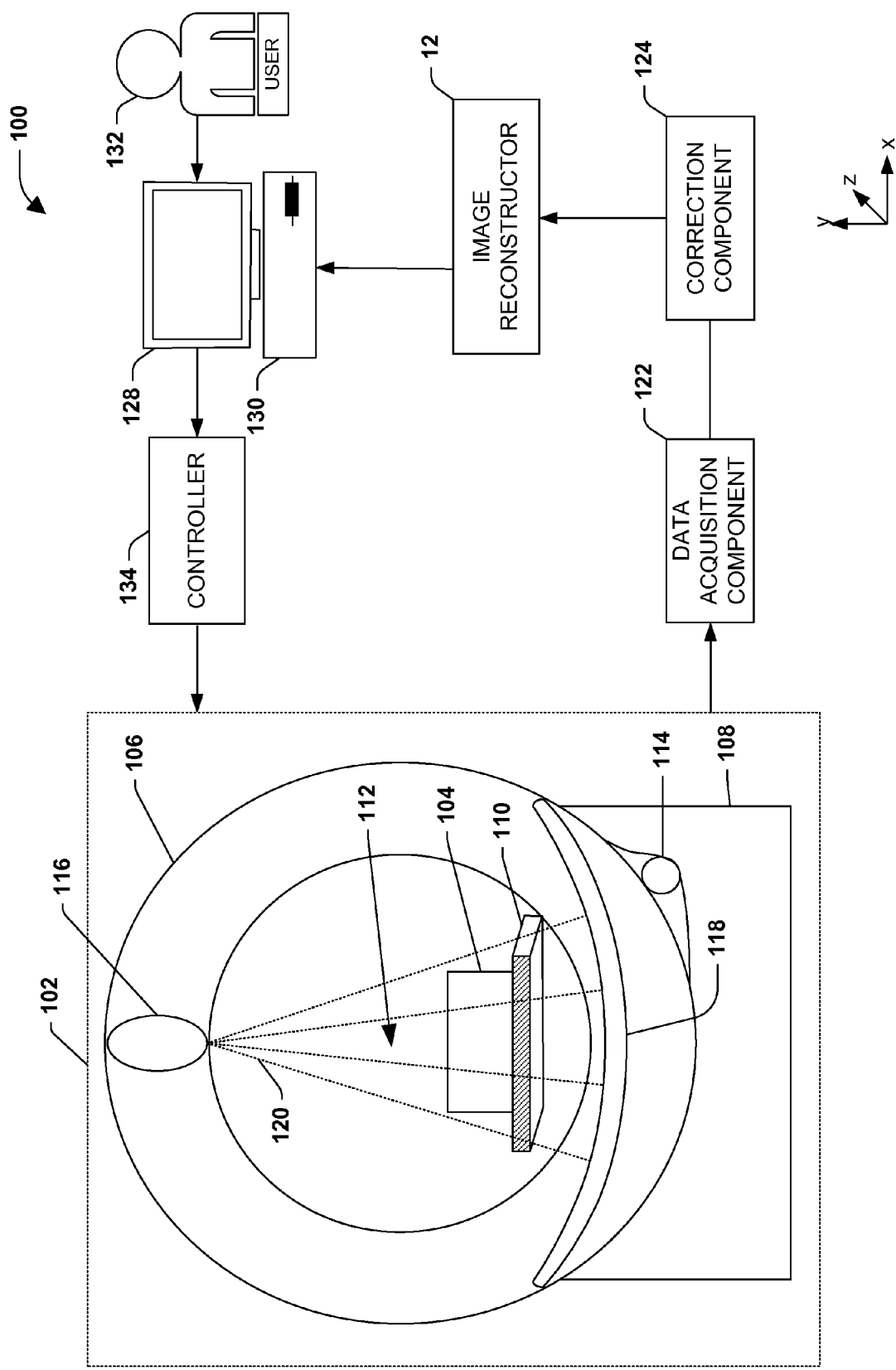
FIG. 1 is a schematic block diagram illustrating an example x-ray examination apparatus.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more detector arrays and/or techniques for manufacturing detector arrays having an effective size that is larger than its actual size are provided. As used herein, the actual size and/or actual area or the like refer to a size/area of a detection surface (e.g., a surface facing a radiation source of the x-ray examination apparatus) at the time of manufacturing. Thus, for example, if one or more pixels were to go bad on the detector array and/or if some material that comprises the detector array were to get damaged (e.g., scratched), the actual size/area of the detector array would not be reduced as a result of the defective pixel and/or as a result of the damage. The effective size and/or effective area or the like refer to the measured area (e.g., after interpolation and/or other correction is applied). Thus, for example, the measured area may comprise portions of the detector array that make up the actual area (e.g., portions that detect radiation and generate electric charge therefrom) and dead spaces (e.g., portions that do not detect/measure radiation).

FIG. 1 is an illustration of an example environment 100 of an x-ray examination apparatus in which data that is generated from components in an x-ray system 102 (e.g., which comprises a flat panel, digital detector array or other digital detector array) may be acquired so that one or more images of an object 104 under examination may be produced and displayed on a monitor 128, for example, such as for viewing by a human user 132 (e.g., radiologist, security personnel, etc.). Such a system 102 may be used to diagnose medical conditions (e.g., broken bones) in a human patient at a medical center or in an animal at a veterinary clinic, and/or to identify objects of interest (e.g., potential threat objects, banned objects, etc.) associated with (e.g., comprising, comprised within, etc.) an object 104 (e.g., luggage) under examination at a security checkpoint, for example. In another embodiment, no image is generated, but, depending at least in part on an acquisition modality, a density (or some other object physico-chemical property) of respective objects (or aspects or parts thereof) can be identified and compared with a list of density, effective Atomic number, etc. properties associated with predetermined items (e.g., banned items such as explosives or weapons) to determine if the object 104 potentially comprises one or more of the predetermined items.

It will be appreciated that while a single energy CT scanner is, at times, described herein, the instant application is not intended to be so limited. That is, to the extent possible, the instant application, including the scope of the claimed subject matter, is intended to be applicable to other systems as well. For example, the claimed subject matter is intended to be applicable to other x-ray systems, such as, projection radiography, line scanners, multi-energy CT scanners, etc. It will also be appreciated that the example environment 100 merely illustrates an example schematic and is not intended to be interpreted as necessarily specifying the orientation/position of the components described herein. For example, a data acquisition component 122 as illustrated in FIG. 1, may be part of a rotating gantry 106 portion of the x-ray system 102, or rather, may be part of a detector array 118 of the x-ray system 102.

In the example environment 100, the x-ray system 102 can be configured to examine one or more objects 104 (e.g., a human patient, a series of suitcases at an airport, lumber at a lumber mill, etc.). The x-ray system 102 can comprise a rotating gantry portion 106 and a stationary portion 108. During an examination of the object(s) 104, the object(s) 104 can be placed on a support article 110, such as a bed or conveyor belt, that is selectively positioned in an examination region 112 (e.g., a hollow bore in the rotating gantry portion 106), and the rotating gantry portion 106 can be rotated about the object(s) 104 by a rotator 114 (e.g., motor, drive shaft, chain, etc.).

The rotating gantry portion 106 may surround a portion of the examination region 112 and comprises a radiation source 116 (e.g., an ionizing or non-ionizing radiation source) and a detector array 118 that is mounted on a substantially diametrically opposite side of the rotating gantry 106 relative to the radiation source 116.

During an examination of the object(s) 104, the radiation source 116 emits radiation 120 towards the object(s) 104 under examination while the rotating gantry portion 106 (including the radiation source 116 and/or the detector array 118) rotates about the object(s) 104. Generally, in a CT scanner, the radiation 120 is emitted substantially continuously during the examination. However, in some CT scanners and/or in other imaging devices (e.g., pulsating scanners), the radiation 120 may be pulsed or otherwise intermittently applied during the examination.

As the radiation 120 traverses the object(s) 104, the radiation 120 may be attenuated differently by different parts of the object(s) 104. Because different parts attenuate the radiation 120 differently, an image may be produced based upon the attenuation, or rather indirectly from it based on the variations in the number of radiation photons that are detected by the detector array 118. For example, more dense aspects of the object(s) 104, such as a bone or metal plate, for example, may attenuate more of the radiation 120 (e.g., causing fewer radiation photons to strike the detector array 118) than less dense materials, such as skin or clothing.

In some embodiments, while the object(s) 104 is being examined, the object(s) 104 may be translated along an axis traveling in the z-dimension (e.g., into and out of the page if, as illustrated, the rotating gantry 106 is configured to rotate in an x, y plane). In this way, an object 104 that has a z-dimension greater than the z-dimension of the radiation 120 traversing the object may be examined more quickly (relative to a step-and-shoot scanning approach). It will be appreciated that if the object(s) 104 is being translated (e.g., in the z direction) during an examination while the rotating gantry 104 is rotating (e.g., in the x, y plane), the examination may be referred to as a helical or spiral scan.

The detector array 118 is generally comprised of one or more channels, which may also be referred to herein as detector channels or pixels, configured to convert the radiation into electric charge and to measure the amount of charge produced within a given space. Based upon an addressing scheme corresponding to the channel locations, the detected radiation can be mapped (e.g., it can be determined which part of the object(s) 104 the detected radiation traversed).

As will be discussed in more detail with respect to later figures, the detector array 118 has an effective size (e.g., a measurement size) that is larger than its actual size. Stated differently, one or more detection surfaces (e.g., surfaces facing the radiation source 116) are smaller than the area that is actually being used to create an image(s) of the object under examination.

Figure 3:
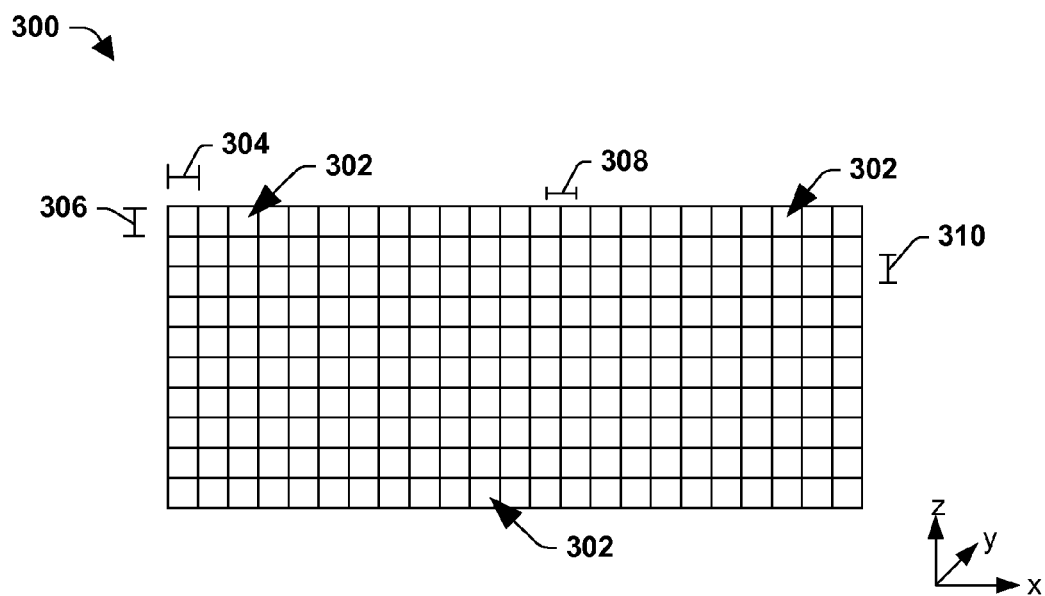
FIG. 3 illustrates a top-down view of a prior art detector array.

In one embodiment, the actual size of the detector array is smaller than its effective size by strategically placing one or more dead spaces (e.g., not configured to detect/measure radiation) within the detector array 118. For example, the channels and the dead spaces may be arranged in a checkerboard pattern such that respective channels are adjacent to one or more dead spaces. In such an embodiment, the channels and the dead spaces may have similarly sized detection surfaces (e.g. a similar x-dimension and a similar z-dimension). Thus, in one embodiment, where the checkerboard pattern continues substantially throughout an entire detection surface of the detector array 118, the actual area of a detection surface of the detector array 118 may be roughly one half the effective size of the detector array 118. It will be appreciated that in such an embodiment (e.g., where the channels and dead spaces are scattered across a detection surface (e.g., creating what may be referred to as a sparse array), the total number of channels (e.g., the total number of active pixels that are detecting radiation and/or measuring electric charge), may be reduced relative to the total number of channels that are commonly found in a prior art detector array of comparable size (e.g., as illustrated in FIG. 3). For example, where a 1 meter by ½ meter array may, in a prior art detector array, comprise 500,000 channels (e.g., where there are substantially no dead spaces between pixels), a similarly sized detector array 118 as described in this embodiment may comprise 250,000 channels. Moreover, the pitch (e.g., the distance between the centers of two adjacent channels) may be increased relative to a prior art detector array. For example, whereas a prior art detector array may have a pitch of about 1 mm (e.g., assuming the channels are 1 $mm^2$), the pitch of a detector array 118 as described in this embodiment may be approximately 2 mm (e.g., still assuming the channels are 1 $mm^2$). It will be also appreciated that techniques for compensating for the dead spaces are discussed herein, such as with respect to a correction component 124, for example.

In another embodiment, the actual size of the detector array 118 is smaller than its effective size by shrinking a detection portion of at least some of the channels. That is, at least some of the detection portions of at least some of the respective channels of the detector array 118 are comprised of a dead space and a detection portion, the dead space being adjacent at least one exterior edge of the channel. Thus, in one embodiment, where the dead space is on all four sides of respective channels, the dead space may surround the detection portion (e.g., such that the detection portion is essentially an island in the center of the channel not contacting any exterior edge of the channel). Referring back to the example of the prior art detector array as described in the preceding paragraph and comparing the prior art detector array to the detector array 118 as described in this embodiment, obvious distinctions may be identified (e.g., between this embodiment, the embodiment described in the previous paragraph, and a prior art detector array). For example, because the size (e.g., detection surface area) of the respective channels is not changed (e.g. but merely a detection portion of the respective channels is reduced), the total number of channels in a detector array 118 as described herein may be the same as the total number of channels in a prior art detector array. For example, a prior art detector array and a detector array 118 as described in this embodiment, measuring approximately 1 meter by ½ meter, may respectively comprise approximately 500,000 channels. Moreover there may be no difference in the pitch of the prior art detector array as compared to the detector array 118 as described in this embodiment because the spacing between adjacent detector channels (e.g., as measured from the center of one channel to the center of another, adjacent channel) is not affected. However, because at least some of the detection portion of at least some of the respective channels are comprised of a dead space (which does not detect/measure radiation), the actual size of the detector array 118 is less than its effective size. It will be appreciated that techniques for compensating for the dead space(s) of respective channels are discussed herein, such as with respect to a correction component 124, for example.

In yet another embodiment (e.g., where the detector array is an indirect conversion detector array), the actual size of the detector array 118 may be smaller than its effective size, by using focusing mechanisms (e.g., microlenses) configured to focus light, for example, generated by a first detection material (e.g., a scintillator material) towards a second detection material (e.g., a photodetector, or collectively, a photodetector array) having a detection surface with an area that is smaller than an area of a detection surface of the first detection material. That is, for example, one or more microlenses, for example, may be situated between a scintillator material, for example, and a photodetector array. As will be described in more detail below, light generated by the scintillator material may be focused (e.g., guided) towards a photodetector array (e.g., comprised of a plurality of photodetectors) having a smaller detection surface area. Thus, an area of the detection surface of the scintillator material may be the same as an area of the detection surface of the scintillator material in a prior art detector array. However, the area of the detection surface of the photodetector array may be smaller than an area of the detection surface of the photodetector array in a prior art detector array. Moreover, it will be appreciated to those skilled in the art that because substantially all of the emitted radiation (e.g., or substantially all of the primary radiation) is detected by the scintillator material, in an embodiment of the detector array 118 that merely comprises focusing mechanisms (e.g., microlenses), no correction may be performed, and thus, in one embodiment, the correction component 124 may be unnecessary, for example. Where this embodiment (e.g., microlenses) is combined with other embodiments (e.g., dead spaces and/or reduced detection portions), however, correction may still need to be performed.

It will be appreciated that, unless otherwise indicated, the example embodiments of the detector array 118 are not intended to be limited to a particular type and/or shape of digital detector array. For example, the detector array 118 may be a direct conversion detector array and/or an indirect conversion detector array, which generally differ in, among other things, how the radiation is converted into electric charge. Generally, direct conversion detector arrays are configured to convert the impinging radiation directly into electric charge using a direct conversion material such as a semiconductor crystalline material (e.g., Cadmium Zinc Telluride, Cadmium Telluride, etc.) and/or an amorphous material, such as amorphous Selenium, for example. Conversely, indirect conversion detector arrays are configured to convert the impinging radiation into another medium, such as light, for example, using a scintillator material, for example, and the electric charge is generated based upon the detection of the other medium (e.g., based upon the amount of light that is detected) using a photodetector (e.g., a photodiode), for example. Moreover, the detector array 118 may be a two-dimensional, flat panel detector array, a curved detector array (e.g. which typically forms a cylindrical or spherical surface, or an arc), or any other shaped detector array known to those skilled in the art.

Radiation 120 that impinges a channel(s) of the detector array 118 generally creates an electric charge(s) that may be detected by a detection/measurement portion of the channel (e.g., by a thin-film transistor, complementary metal-oxide-semiconductor, or other electric component that is configured to collect and/or measure electric charge). Respective channels generate a signal proportional to the electric charge detected (e.g., which was generated based upon the impinging radiation), and such signals are fed to a data acquisition component 122 (e.g., which may be integral with the x-ray system 102 or with the detector array 118). Because the electric charge detected by the one or more channels is directly related to the number of detected radiation photons or integrated energy of the detected photons, the output is indicative of the attenuation of the radiation 120 as it traversed the object(s) 104. It will be appreciated that, in one embodiment, when a channel is not collecting/measuring electric charge, the channel may produce a baseline signal that indicates that the channel has detected no electric charge. In yet another embodiment, no signal may be generated by a channel unless and/or until an electric charge is detected.

It will be appreciated that other features of the detector array 118 and/or the radiation source 116 may be apparent from the remaining figures of the instant application. For example, as will be described below, the radiation source 116 may be configured to shift its focal spot (e.g., the spot from which radiation is emitted)) and/or the detector array 118 may be shifted by ¼ of a detector channel (e.g., relative to a center beam of radiation that traverses an axis of rotation of the rotating gantry) (e.g., in the x-direction) to account for various detector array characteristics, for example.

The data acquisition component 122 is configured to collect information and/or data related to radiation that was detected by the detector array 118. For example, in one embodiment, the data acquisition component 122 is configured to receive analog signals generated by the detector array 118, which are indicative of the detected radiation, and to convert the analog signals into the digital domain using analog-to-digital techniques known to those skilled in the art. Moreover, the data acquisition component 122 may be configured to compile the digital data (e.g., yielded from a plurality of channels of the detector array 108) into one or more projection images.

The example environment 100 further comprises a correction component 124 configured, in some embodiments, to correct for the difference between the actual area of a detection surface of the detector array and its effective area. For example, the correction component 124 may be configured to use interpolation and/or other analytical and/or iterative techniques known to those skilled in the art to correct for a sparse detector array (e.g., where information from channels adjacent a dead space are used to estimate/predict what the dead space would have measured had the dead space been an active channel configured to detect/measure radiation). In another embodiment, the correction component 124 may be configured to use information collected from the detector array 118 at a position approximately 180 degrees away from the position of the detector array 118 that yielded the information that is being corrected to correct for dead space in the detector array and/or in respective channels. Stated differently, where the detector array 118 is shifted with respect to an isocenter of the system (e.g., by a quarter of a detector channel in the x-dimension), information yielded while the detector array 118 is at a second position relative to the object 104 under examination can be used to complement the information/data (e.g., the projection data) yielded while the detector array 118 was at a first position. For example, if the shift of the detector array is approximately ¼ of the channel, the projections 180 degrees apart in gantry rotation can be ½ of a channel apart in terms of sampling the object. It will be appreciated that the channel definition can be one physical channel, or a combination of a channel and dead space. In yet another embodiment, the correction component is configured to use information collected from radiation emitted from two different locations on a radiation source (e.g., and indicative of a same view of the object 104) to correct for dead space in the detector array and/or in respective channels. Stated differently, where the focal spot is shifted during the examination (e.g., in either the x-direction or in the z-dimension), information representing a single view of the object, a portion of which is representative of radiation emitted from a first location and a portion of which is representative of radiation emitted from a second location on the radiation source, may be used to correct for dead space in the detector array and/or in respective channels.

It will be appreciated that while the correction component 124 is described herein as correcting projection data yielded from the data acquisition component 122, the scope of the claims and the instant application are not intended to be so limited. That is, to the extent possible, the correction component 124 may be positioned at a different location along a pathway of the conversion of signals into images and may correct different types of data. For example, in another embodiment, the correction component 124 may be positioned after the image reconstructor 126 and may be configured to correct image data (e.g., as opposed to projection data). In yet another embodiment, the correction component 124 may not be a standalone component, but rather may be part of a data acquisition component 122, for example.

The example environment 100 also comprises an image reconstructor 126 configured to receive the projection data from the data acquisition component 122, and/or, in the illustrated embodiment, receive corrected projection data from the correction component 124. The image reconstructor 126 is also configured to generate one or more x-ray images that are more understandable by a user 132 viewing the x-ray image(s) relative to the projection data. Stated differently, the image reconstructor 126 is configured to convert the images from projection space to image space using suitable analytical, iterative, and/or other image reconstruction techniques known to those skilled in the art (e.g., 2D filtered backprojection, tomosynthesis reconstruction, etc.).

Images that are reconstructed by the image reconstructor 126 are transmitted to a workstation 130 (e.g., a computer terminal) configured to receive image(s) that can be displayed on a monitor 128 to the user 132 (e.g., medical personnel, security personnel, etc.), for example. A user 132 can thus inspect the image(s) to identify areas of interest within the object(s) 104. The workstation 130 can also be configured to receive user input which can direct operations of the x-ray system 102 (e.g., radiation dose, speed of rotation, etc.), for example.

In the example environment 100, a controller 134 is operably coupled to the workstation 130. In one example, the controller 134 is configured to receive user input from the workstation 130 and generate instructions for the x-ray system 102 indicative of operations to be performed. For example, the user 132 may want to rescan the object(s) 104 using a different dose or energy of radiation and the controller 134 may issue an instruction instructing the radiation source 106 to emit the desired dose or energy of radiation 110.

Figure 2:
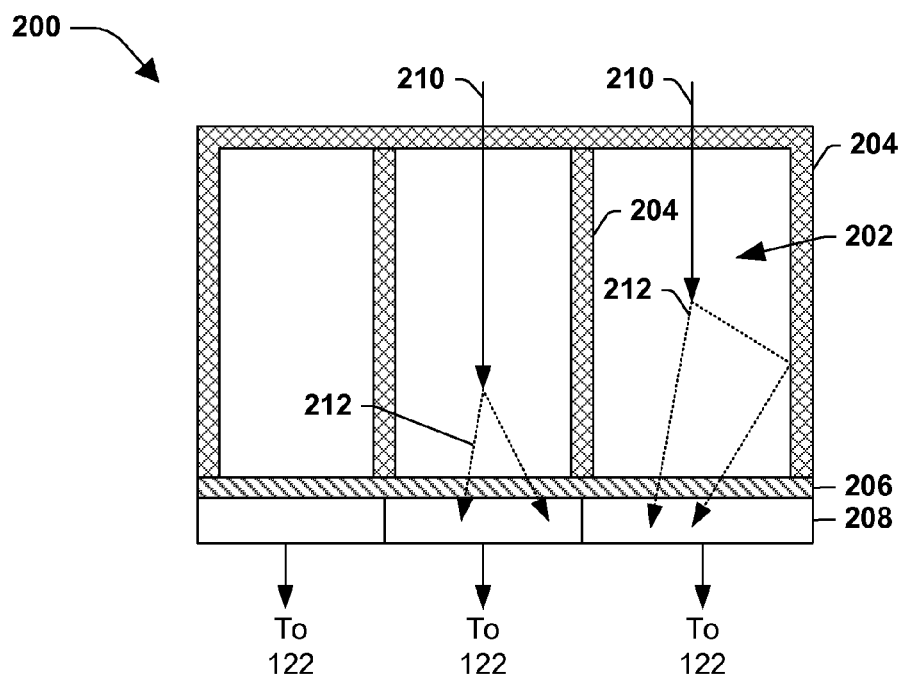
FIG. 2 illustrates a cross-section view of three channels of a prior art, indirect conversion detector array.

FIG. 2 illustrates (e.g., in cross-section) three channels of an example indirect conversion detector array 200 (e.g., 118 in FIG. 1), such as may be found in prior art. Such a detector array 200 may be an imaging detector for mammography scanners, line scanners, CT scanners, and/or other imaging systems, for example. Respective channels of the indirect conversion detector array 200 comprise a scintillator 202 (e.g., housed within sidewalls 204 and a substantially translucent base 206) and a photodetector 208, for example. Incident radiation 210 normally interacts with the scintillator 202, and creates light 212 (e.g., luminescent photons). This light 212 is absorbed in the photodetector 208 and converted into electrical charge, which can be measured by the photodetector 208 or other electronic device configured to detect/measure electric charge.

The scintillator 202 is configured to convert incident radiation 210 into light 212 and can be made of a crystalline material (e.g., Cadmium Tungstate, Zinc Tungstate, Cesium Iodide, etc.), a ceramic material, and/or any other scintillating material known to those skilled in the art. Commonly, such scintillator materials are configured to emit light in the visible spectral range, from about 400 nm to about 600 nm, but it will be appreciated that the scope of the instant disclosure and/or claimed subject matter is not intended to be limited as such. For example, the scintillator may emit light in the spectral range below 400 nm and/or above 600 nm.

The photodetector 208 is configured to create a charge when it is exposed to light. Typically the photodetector is manufactured using crystalline or amorphous silicon, with a built-in electric field of p-n junction which allows separate electric charges, created in the semiconductor by light, to be detected. Stated differently, when light 212 enters the photodetector 208, electrons in the photodetector 208 (e.g., a semiconducting structure) become excited. That is, if the energy of the light 212 is greater than a bandgap energy of the photodetector 208, electrons in the photodetector 208 will move from a valence band onto a conduction band, and electron-hole pairs will be generated. The free electrons created by the electron-hole pairs drift to an edge of the photodetector 208 and can be converted into an output signal(s), which can be output to a data acquisition component (e.g., 122 in FIG. 1).

Respective photodetectors 208 of the detector array 200 can be made of silicon and/or any other photodetector material known to those skilled in the art. For example, in one embodiment, the photodetector 208 is made out of a high resistivity silicon wafer, between about 250 μm to 500 μm thick, and is manufactured using planar technology known to those skilled in the art.

While the composition of a direct conversion detector array is not illustrated herein, it will be appreciated that its structure is similar to the structure of the indirect conversion detector array, but with different materials. For example, the scintillator material 202 is replaced with a direct conversion detector material, such as Cadmium Zinc Telluride, Cadmium Telluride, Lead Iodide, Mercury Iodide, doped amorphous Selenium and/or amorphous Silicon, for example. Moreover, because the direct conversion detector array is configured to convert the radiation directly into electric charge (e.g., as opposed to light or another medium), a photodetector 208 is not necessary. Thus, respective channels of a direct conversion detector array may merely comprise a direct conversion detector material and a thin-film transistor, for example (e.g., as opposed to a scintillator 202 and a photodetector 208 as comprised in an indirect conversion channel). It can be appreciated that materials comprised in direct and/or indirect detector arrays have an associated cost and a reduction in at least some of said materials, as provided herein, will thus result in, among other things, a cost reduction.

FIG. 3 illustrates a top-down view of an example prior art detector array 300 (e.g., 118 in FIG. 1). That is, FIG. 3 illustrates a view of the detector array 300 from the perspective of a radiation source (e.g. 116 in FIG. 1). It will be appreciated that from such an angle, the features of an indirect conversion detector array and the features of a direct conversion detector array are virtually indistinguishable. Thus, the example prior art detector array 300 could be a direct conversion detector array or an indirect conversion detector array.

As illustrated, the example detector array 300 is comprised of a plurality of channels 302 respectively configured to detect radiation impinging a particular portion of the detector array 300. Respective channels 302 have a predefined x-dimension 304 and a predefined z-dimension 306. Generally, the x-dimension 304 and the z-dimension 306 of respective channels 302 is substantially equal, but they may differ. For example, in one embodiment, the dimensions 304, 306 are substantially equal to 1 millimeter. Thus, an area of a detection surface of a channel (e.g. a surface facing the radiation source) may be said to be 1 mm$^2$.

It will be appreciated that the dimensions 304, 306 of the channels 302 may vary according to the application and/or the desired resolution of images resulting from the examination. For example, a detection surface of respective channels 302 of detector arrays found in security and/or industrial applications may have a greater area than the detection surface of respective channels 302 of detector arrays found in medical applications because a lower resolution image may be acceptable in security and/or industrial application than what is acceptable in medical applications.

It will be appreciated that, as illustrated in the example prior art detector array 300, adjacent channels 302 generally directly abut one another such that there is little, if any, dead space (e.g., where radiation that impinges the detector array is not detected/measured) between adjacent channels 302. That is, substantially all of the radiation emitted from the radiation source is detected by one of the channels (e.g., as long as it is not scattered before reaching the detector array 300). Thus, in a prior art detector array 300 there is little, if any, dead space wherein radiation can impinge the detector array 300 without being detected by one or more channels (e.g., there is little to no dead space in the detector array).

Moreover, the pitch, which is measured as the distance between the center of a first channel and the center of an adjacent channel, in the x-dimension 308 and the pitch in the z-dimension 310 are substantially equal to the x-dimension 304 and the z-dimension 306 of the respective channels in the prior art detector array 300. For example, where the x-dimension 304 of respective channels 302 is 1 mm, the pitch in the x-dimension 308 may be approximately 1 mm, and where the z-dimension 306 of respective channels 302 is 1 mm, the pitch in the z-dimension 310 may be approximately 1 mm. In this manner, the active and effective sizes of the array 300 can be said to be equal.

FIGS. 4 through 8 illustrate top-down views of example detector arrays 400, 500, 600, 700, 800 (e.g., 118 in FIG. 1), wherein a number of the channels are replaced with a dead space. It will be appreciated that for purposes of clarity, detector arrays comprising dead space that take the place of channels may be referred to as sparse array detectors, sparse detector arrays, and the like. It will also be appreciated that such detector arrays 400, 500, 600, 700, 800 may be either direct conversion detector arrays or indirect conversion detector arrays. As will be appreciated the effective size of these arrays 400, 500, 600, 700, 800 can be said to be larger than their actual size.

Figure 4:
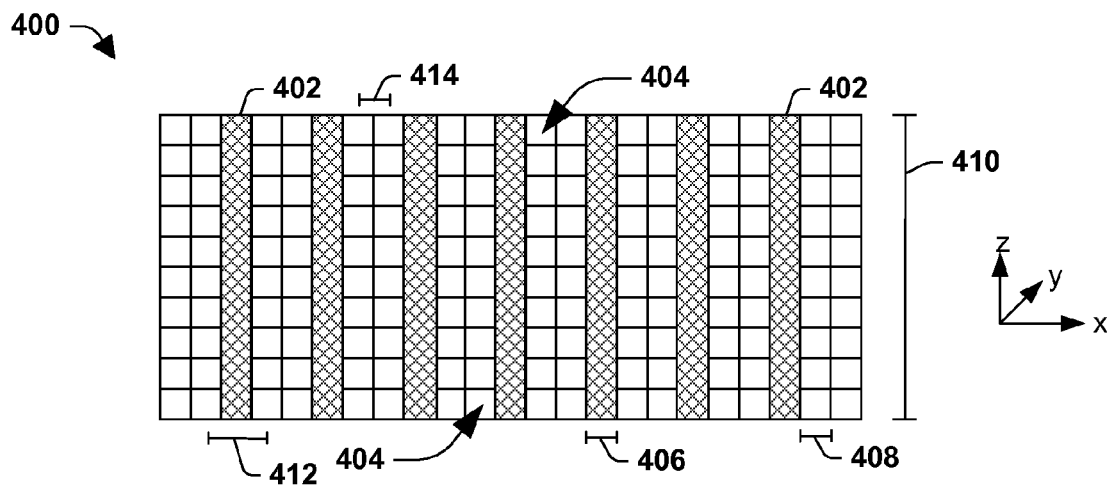
FIG. 4 illustrates a top-down view of an example sparse array detector.

FIG. 4 illustrates a first embodiment of a sparse array detector. Specifically, FIG. 4 illustrates a detector array comprising columns of channels 404, at least some of which are separated from an adjacent column by dead space 402. Radiation that impinges the dead space 402 is not detected/measured (e.g., and thus is not used to generate an image of an object under examination). In one embodiment, the dead space 402 comprises a filler material, such as lead, loaded oxides, and/or other materials having properties suited for absorbing radiation, for example. Such filler materials are generally less costly than materials used to detect radiation.

In the example embodiment, the x-dimension 406 of the dead space 402 is substantially equal to the x-dimension 408 of respective channels 404. Stated differently, the width of the dead space 402 is substantially equal to the width of the channels 404. However, in other embodiments, the width of the dead space 402 may be different than the x-dimension 408 of the respective channels 404. For example, the x-dimension 406 of the dead space 402 may be twice as large as the x-dimension 408 of respective channels 404. In yet another example, the x-dimension 406 of the dead space 402 may be one half as large as the x-dimension 408 of respective channels 404. Thus, the x-dimension 406 of the dead space 402 may be less than, equal to, or more than the x-dimension 408 of respective channels 404.

Moreover, in the example embodiment of a sparse detector array 400, the z-dimension 410 of the dead space 402 is substantially equal to the depth (e.g. z-dimension) of the detector array 400. However, it will be appreciated that in other embodiments, the z-dimension 410 of the dead space may differ from the depth of the detector array 400. That is, the z-dimension 410 of the dead space may range from a value that is less than the z-dimension of respective channels to a value that is equal to the depth of the detector array 500, for example.

It will be appreciated that due to the dead space 402, the x-dimension pitch 412 of the channels adjacent the dead space 402 (e.g., and separated by the dead space 402) may be different than the x-dimension 408 of the respective channels 404. Moreover, channels that are adjacent one another and not separated by the dead space 402 may have a different x-dimension pitch 414 than channels that are adjacent one another but separated by the dead space 402. For example, in one embodiment, where the channels 404 have an x-dimension 408 substantially equal to 1 mm and the dead space 402 has an x-dimension 406 equal to the x-dimension 408 of the channels 404, the x-dimension pitch 412 of two adjacent channels separated by the dead space 402 may be about 2 mm; whereas the x-dimension pitch 414 of two adjacent channels not separated by a dead space may be about 1 mm.

It will also be appreciated that while, in the illustrated embodiment, at least some adjoining columns of channels are not separated by dead space, in another embodiment, respective column may be separated by dead space (e.g., dead space adjoins each column of channels such that each column of channels is separated from an adjacent column of channels by dead space).

Figure 5:
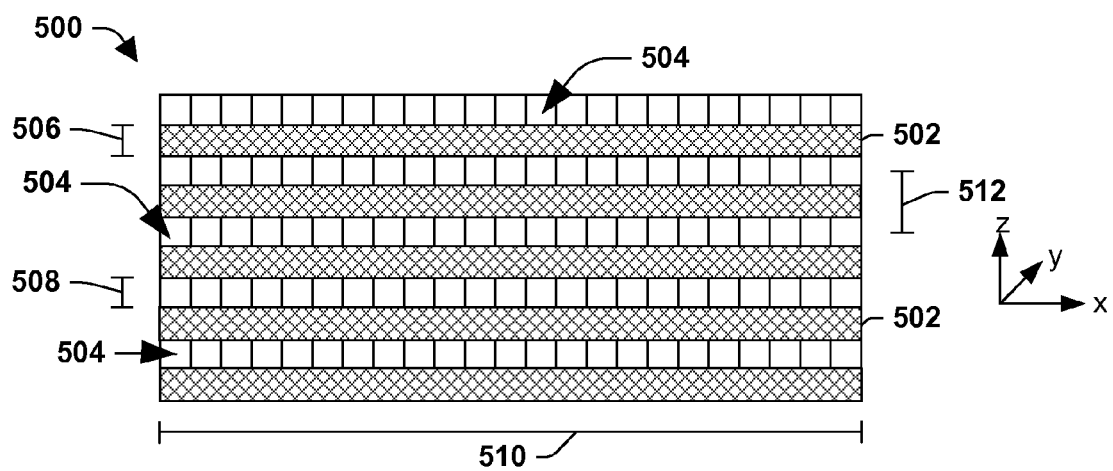
FIG. 5 illustrates a top-down view of an example sparse array detector.

FIG. 5 illustrates a second embodiment of a sparse array detector. Specifically, FIG. 5 illustrates a detector array comprising rows of channels 504, at least some of which are separated from an adjacent row by dead space 502. Radiation that impinges the dead space 502 is not detected/measured (e.g., and thus is not used to generate an image of an object under examination).

In the example embodiment, the z-dimension 506 of the dead space 502 is substantially equal to the z-dimension 508 of respective channels 504. Stated differently, the depth of the dead space 502 is substantially equal to the depth of the channels 504. However, in other embodiments, the z-dimension 506 of the dead space 502 may differ from the z-dimension 508 of the respective channels 504. For example, the z-dimension 506 of the dead space 502 may be twice as large as the z-dimension 508 of respective channels 504. In yet another example, the z-dimension 506 of the dead space 502 may be one half as large as the z-dimension 508 of respective channels 504. Thus, the z-dimension 506 of the dead space 502 may be less than, equal to, or more than the z-dimension 508 of respective channels 504.

Moreover, in the example embodiment of a sparse detector array 500, the x-dimension 510 of the dead space 502 is substantially equal to the width (e.g. x-dimension) of the detector array 500. However, it will be appreciated that in other embodiments, the x-dimension 510 of the dead space may differ from the width of the detector array 500. That is, the x-dimension 510 of the dead space 502 may range from a value that is less than the x-dimension of respective channels to a value that is equal to the width of the detector array 500, for example.

It will be appreciated that due to the dead space 502, the z-dimension pitch 512 of the channels adjacent the dead space 502 (e.g., and separated by the dead space 502) may be different from the z-dimension 508 of the respective channels 504. For example, in one embodiment, where the channels 504 have a z-dimension 508 substantially equal to 1 mm and the dead space 502 has a z-dimension 506 equal to the z-dimension 508 of the channels 504, the z-dimension pitch 512 of two adjacent channels separated by the dead space 502 may be about 2 mm.

It will also be appreciated that while, in the illustrated embodiment, respective rows of channels 504 are separated by dead space 502, in another embodiment, there may be little to no dead space 502 between two or more rows of channels 504. That is, two or more rows of channels may be directly abut one another and may not be separated by dead space 502 or may be separated by a nominal amount of dead space 502, for example.

Figure 6:
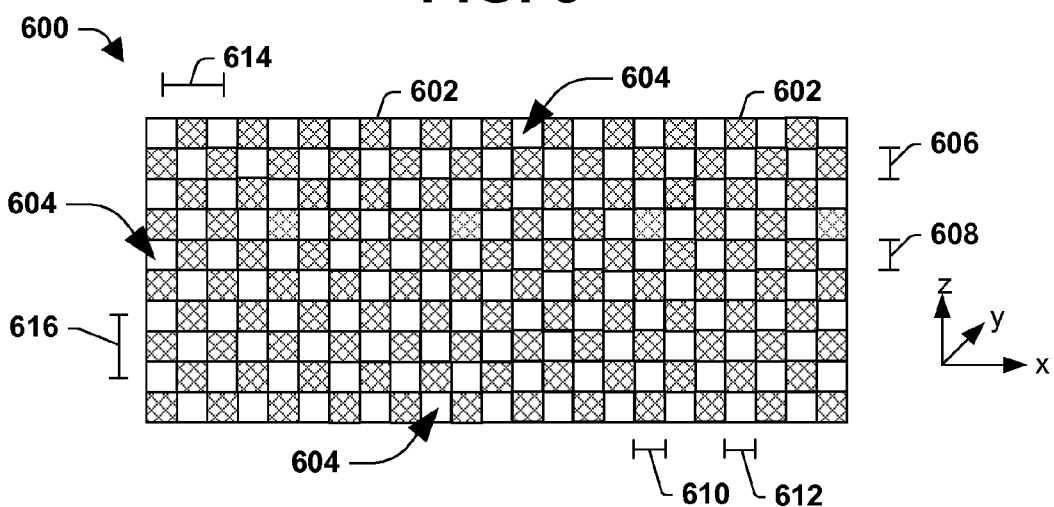
FIG. 6 illustrates a top-down view of an example sparse array detector.

FIG. 6 illustrates yet another embodiment of a sparse array detector 600. Specifically, FIG. 6 illustrates a detector array 600 comprising a checkerboard pattern of channels 604 and dead spaces 602. Radiation that impinges the dead space 602 is not detected/measured (e.g., and thus is not used to generate an image of an object under examination).

In such an embodiment, the z-dimension 606 of the dead space 602 is generally substantially equal to the z-dimension 608 of respective channels 604, and the x-dimension 610 of the dead space 602 is generally substantially equal to the x-dimension 612 of respective channels 604. Moreover, in such an embodiment, it will be appreciated that the x-dimension pitch 614 and/or the z-dimension pitch 616 may be greater than the x-dimension 612 and z-dimension 608 of the channels 604, respectively. For example, where the channel measures around 1 mm by 1 mm, the x-dimension pitch 614 of the channels 604 may be around 2 mm or more and the z-dimension pitch 616 of the channels 604 may be around 2 mm of more. Thus, in one embodiment, both the x-dimension pitch 614 and the z-dimension pitch 616 of the channels are greater than the x-dimension 612 and the z-dimension 608 of the channels 604, respectively.

Figure 7:
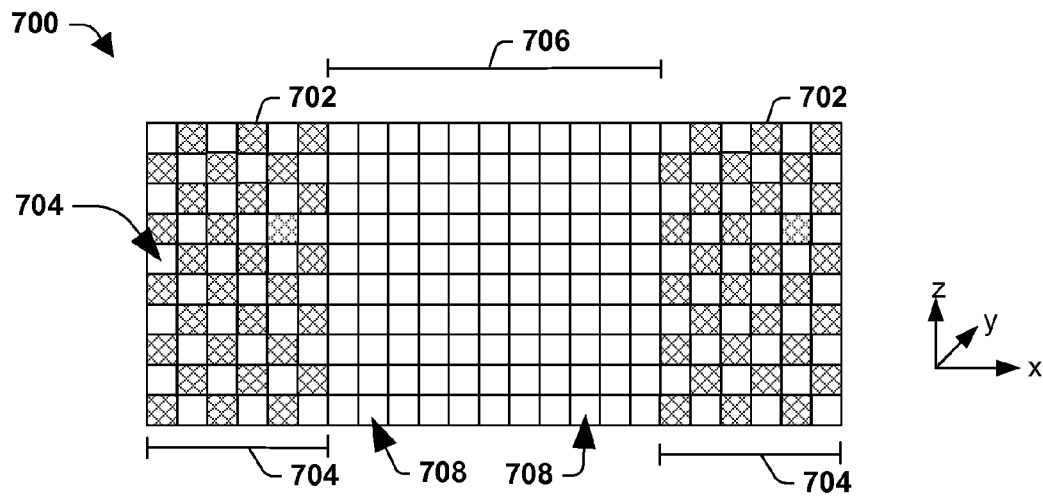
FIG. 7 illustrates a top-down view of an example sparse array detector having a sparse region and a non-sparse region.
Figure 8:
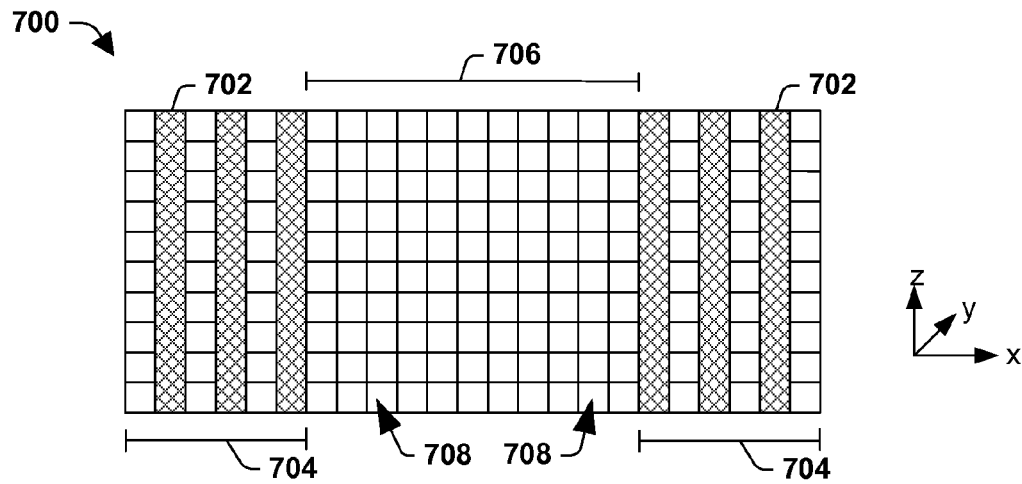
FIG. 8 illustrates a top-down view of an example sparse array detector having a sparse region and a non-sparse region.

It will be appreciated that while FIGS. 4-6 illustrate the dead spaces as continuing substantially throughout the detector arrays 400, 500, 600, the instant application, including the scope of the claims, is not intended to be so limited. For example, as illustrated in FIGS. 7-8, merely one or more portions 704, but not all, of the detector array 700 (e.g., 118 in FIG. 1) may comprise dead space 702 (e.g., 602 in FIG. 6). One or more other portions 706 may be comprised substantially, entirely of channels 708 (e.g., 604 in FIG. 6) configured to detect/measure impinging radiation. Thus, there may be one or more sparse regions and one or more uniform or non-sparse regions of the detector array 700.

In one example, where the detector array 700 is comprised in a CT scanner, the sparse regions and the uniform regions may be defined based upon a field of view, or scan circle that defines the extent of the examination region that is imaged by the detector array (e.g. which may be defined as a portion of the examination region that is substantially continuously exposed to radiation during an examination). Stated differently, portions of the detector array 700 that detect radiation which traverses the field of view may be uniform (e.g., comprised substantially entirely of channels 708), and portions of the detector array 700 that detect radiation which has not traversed the field of view (e.g., but is still within the scanning field) may be sparse (e.g. comprised of both channels 708 and dead space 702, or all dead space). In this way, for example, an interior portion (e.g., 706) of the detector array 700, where the spatial resolution tends to be greater, comprises a uniform region, and exterior edges (e.g., 704) of the detector array 700, where the spatial resolution tends to be less, comprise sparse regions. Thus, even with little to no correction for sparse regions, less costly sparse detector arrays may be implemented with little to no effect on spatial resolution and/or image quality.

Figure 9:
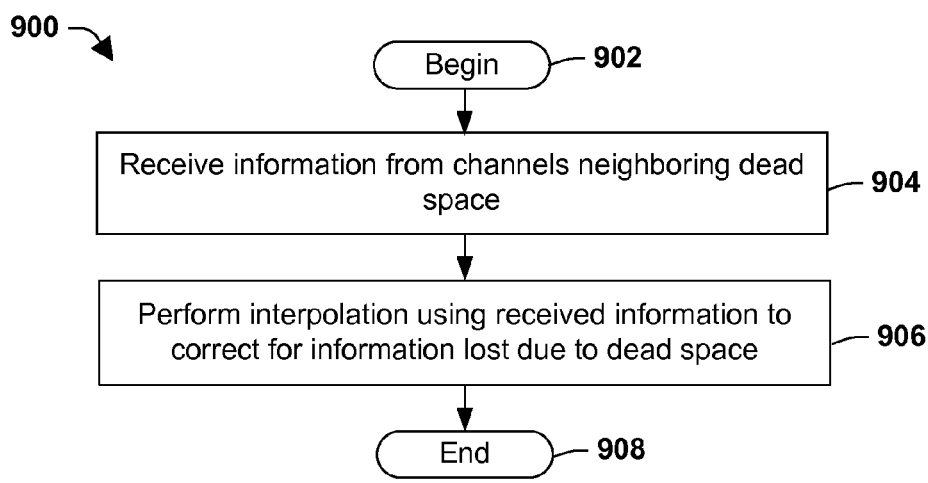
FIG. 9 illustrates a flow diagram illustrating an example method for correcting for the difference between an actual size of a detector array and its effective size.

FIG. 9 illustrates an example method 900 for correcting projection data and/or image data when the detector array (e.g., 118 in FIG. 1) comprises one or more sparse regions (e.g., as illustrated in FIGS. 4-8). Such an example method 900 may be, at least in part, performed by a microprocessor of a correction component, such as the correction component 124 in FIG. 1, for example.

The method begins at 902 and information from channels (e.g., 708 in FIGS. 7-8) neighboring dead space (e.g., 702 in FIGS. 7-8) is received at 904. That is, the projection data and/or the image data yielded from channels that are neighboring, adjacent too, etc. the dead space is received (e.g., by the correction component 124 in FIG. 1, for example). It will be appreciated to those skilled in the art that because respective channels are mapped to a specific portion of the detector array, it may be a relatively simple matter to identify projection data and/or image data yielded from channels neighboring the dead space. That is, techniques for identifying information yielded from specific channels (e.g., channels neighboring the dead space) are known to those skilled in the art and are contemplated herein. Thus, information yielded from channels of interest (e.g., neighboring channels) may be segmented, isolated, or otherwise distinguished from information yielded from channels that are not of interest.

At 906 in the example method 900, an interpolation is performed using the received information to correct for information lost due to the dead space (e.g., which was intentionally created in the detector array and did not merely occur due to a failure of an electronic component and/or an error that occurred during manufacturing). Stated differently, analytic, iterative, or other correction techniques which estimate or approximate the amount of radiation that would have been detected/measured in a dead space had a channel replaced the dead space may be used to compensate for the dead space. For example, in one embodiment, techniques similar to those presently used to compensate for a dead channel (e.g., a channel that has malfunctioned and is no longer operating properly) may be used. In this way, holes in the data that are created due to the dead space (e.g., or the bad channel) may be filled in based upon information yielded from the interpolation, for example.

At 908, the example method 900 ends. That is, the information, including the information acquired from the interpolation related to the dead space, is sent to an image reconstructor and/or is used to correct the image data (e.g., if the example method 900 is performed on image data that has already been generated by an image reconstructor, as opposed projection data that has not yet been converted to image data). Stated differently, if the example method 900 is performed prior to image reconstruction, the information from the respective channels and information acquired from the interpolation (e.g., which may be in projection space) can be sent to an image reconstructor that is configured to use the received information (e.g., including the information yielded from the channels and the information yielded from the interpolation) to generate one or more images of an object under examination. If the example method 900 is performed after image reconstruction has taken place, the reconstructed images can be merely corrected based upon the information yielded from the interpolation, for example.

Figure 10:
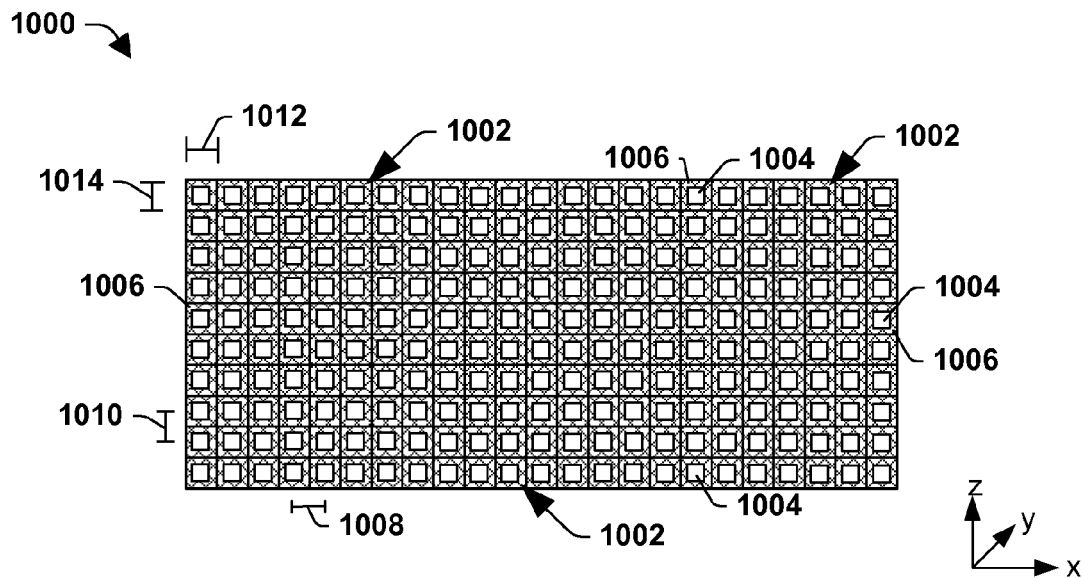
FIG. 10 illustrates a top-down view of an example detector array having channels respectively comprising a detection portion and dead space.

FIG. 10 illustrates a top-down view of yet another example cost effective sparse detector array 1000 (e.g., looking at the detector array 1000 from the view of the radiation source), wherein respective channels 1002 (e.g., 302 in FIG. 3) are comprised of two portions. A first portion 1004 (e.g., which is not shaded) being a detector portion and a second portion 1006 (e.g., which is shaded) comprising dead space. Thus, for at least a portion of the detector array, respective channels comprise a detector portion 1004 and some dead space 1006. Just as described above, radiation that impinges the dead space 1006, which may be filled with some less expensive radiation absorbing material, such as lead and/or load oxides, for example, is not detected/measured. Thus, radiation that strikes the dead space 1006 is not used to reconstruct an image(s) of the object. Conversely, the detection portion 1004 of respective channels 1002 is configured to detect/measure radiation striking thereon and may be used to reconstruct an image(s) of the object.

It will be appreciated that while the example detector array 1000 illustrates each channel 1002 in the detector array 1000 as comprising a detection portion 1004 and some dead space 1006, in another embodiment, fewer than all of the channels 1002 may comprise a detection portion 1004 and some dead space 1006. That is, in another embodiment, the detector array 1000 may comprise some channels 1002 that comprise both a detection portion 1004 and some dead space 1006 and some other channels 1002 that merely comprise a detection portion 1004 (e.g., and/or other channels (not shown) that merely comprise dead space). In such an embodiment, the detection portion 1004 of channels which merely comprise a detection portion 1004 may have a detection surface (e.g., a surface facing the radiation source) that is substantially equal in area to the detection surface of the channel 1002. For example, in one embodiment, where the detector array 1000 is comprised in a CT scanner, channels 1002 comprising both detection portions 1004 and dead space 1106 may be placed on an outer portion(s) (e.g., 704) of the detector array 1000 (e.g., just as the sparse regions were situated on outer edges in FIGS. 7 and 8), and channels 1002 merely comprising detection portions 1004 may be placed on an interior portion (e.g., 706) of the detection array 1000.

Moreover, it will be appreciated that while the example detector array 1000 illustrates dead space 1006 as surrounding the detection portion 1004 of respective channels 1002, the instant application and the scope of the claims is not intended to be so limited to the extent possible. That is, other configurations for arranging a detection portion 1004 and dead space 1006 within a channel are also contemplated, some of which are illustrated in FIGS. 11-13.

Figure 11:
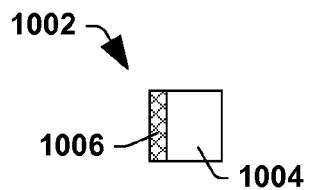
FIG. 11 illustrates a top-down view of an example channel having a sparse region and a non-sparse region.
Figure 12:
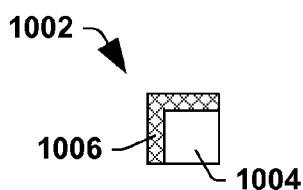
FIG. 12 illustrates a top-down view of an example channel having a sparse region and a non-sparse region.
Figure 13:
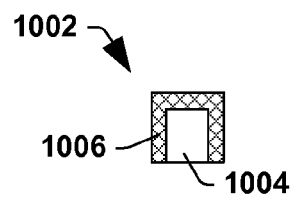
FIG. 13 illustrates a top-down view of an example channel having a sparse region and a non-sparse region.

Specifically, FIGS. 11-13 illustrate a zoomed in, top-down view of a single channel 1002 having dead space 1006 on fewer than all sides of a detector portion 1004. For example, as illustrated in FIG. 11, dead space 1006 may be comprised on merely one side of the channel 1002. Thus, three sides of the detection portion 1004 come into contact with walls of the channel 1002. In another embodiment, as illustrated in FIG. 12, dead space 1006 may be comprised on two sides of the channel 1002, and two sides of the detection portion 1004 come into contact with walls of the channel 1002. In yet another embodiment, as illustrated in FIG. 13, dead space 1006 may be comprised on three sides of the channel 1002, and one side of the detection portion 1004 comes into contact with walls of the channel 1002. Moreover, it will be appreciated that while FIGS. 11-13 illustrate dead space 1006 as being on particular sides of the channel 1002, other configurations are contemplated herein. For example, in FIG. 11, the dead space may be situated above the detection portion 1004, as opposed to on the left side of the detection portion as illustrated herein. That is, any (regular, irregular, ratio, proportion, etc.) arrangement/configuration/design, etc. of dead space and detection portion in a channel is contemplated herein.

Returning to FIG. 10, several aspects of a detector array 1000 having at least some channels that comprise a detection portion 1004 and dead space 1006 should be pointed out for purposes of clarity (e.g., to distinguish the features of the instant detector array 1000 relative to the sparse array (e.g., as illustrated in FIGS. 4-8) and to the prior art detector array (e.g., as illustrated in FIG. 3)). For example, although possible, unlike the sparse array where channels are replaced with dead space, in the embodiments illustrated in FIGS. 10-13, few, if any, channels are replaced with dead space. Thus, for example, whereas a sparse array, as illustrated in FIGS. 4-8, may comprise a total of 250,000 channels, the detector array 1000 as described in the instant embodiment having approximately that same total area as the sparse array may comprise 500,000 channels (e.g., the same number as a prior art detector may comprise). Moreover, the x-dimension pitch 1008 and z-dimension pitch 1010 may be substantially equal to the x-dimension 1012 and the z-dimension 1014 of the channels 1002 (e.g., just as illustrated in FIG. 3 with the prior art detector array). For example, where respective channels 1002 measure around 1 mm by 1 mm in the x- and z-dimensions 1012, 1014, the x-dimension pitch 1008 may be substantially equal to 1 mm and the z-dimension pitch 1010 may be substantially equal to 1 mm. It will be appreciated that this is different than the pitches in a sparse array, which may be larger than the dimensions of the channel due to the dead space (e.g., which replaces a channel) between two adjacent channels, for example.

It will be appreciated to those skilled in the art that in some applications, the dead space 1006 between detection portions 1004 of adjacent channels may result in less effective detector geometric efficiency (e.g., compared with the prior art where detection portions of two channels are substantially adjoining one another). Thus, in some embodiments, in order to satisfied Nyquist criteria (e.g., that the sampling frequency must be at least twice the highest frequency of the object), a flying focal spot may be used and/or the detector array may be mounted such that it is shifted by a quarter detector in the x-dimension (e.g., relative to a center beam of radiation that traverses an axis of rotation). Stated differently, in some embodiments, such an in CT applications, to satisfy Nyquist criteria, one or more techniques may be used to increase sampling frequency.

For example, in one embodiment, to satisfy Nyquist criteria, the radiation source is configured to shift the focal spot (e.g. by approximately one millimeter) during a rotation about the object. In doing so, the object is viewed twice as frequently. That is, within a given period of time that typically makes up one view, two samples may be acquired. A first sample may represent radiation emitted from a first location on the radiation source and detected with the given period of time that makes up the view, and a second sample may represent radiation emitted from a second location on the radiation source and detected within substantially the same, given period of time.

In another embodiment, to satisfy Nyquist criteria, the detector array is shifted by one quarter of the x-dimension 1012 of the channels 1002 relative to a center beam of radiation that passes from the focal spot of the radiation source through an axis of rotation for a rotating gantry portion (e.g., 106 in FIG. 1) of an x-ray scanner (e.g., 102 in FIG. 1), for example. Such a shift is commonly referred to by those skilled in the art as a quarter-detector shift. Thus, the center of the detector array 1000 is not aligned with the center beam of radiation. In this way, the sample radius for a given channel is shifted by half a channel width in a 180 degree orientation, and therefore sampling frequency within a full scan is doubled.

It will be appreciated that in one embodiment, the amount of dead space 1006 that is permissible between detection portions 1004 of adjacent channels while satisfying Nyquist criteria may depend upon whether the flying focal spot and/or quarter-detector shift techniques are used. For example, while it is known that having no dead space between detector portions 1004 of channels may improve image quality, the respective channels may comprise some dead space (e.g., without significantly degrading image quality) if the dead space is corrected using at least one of focal spot shift, quarter-detector shift and/or one or more other correction techniques.

In yet another embodiment, where both focal spot shifting and a quarter-detector shift are used, the dead space 1004 between adjoining channels may be increased to full channel dimension, for example, while satisfying the Nyquist criteria. Stated differently, by using both the focal spot shifting technique and the quarter-detector shift technique, the detection portion 1004 can be reduced even further (e.g., relative to its size if merely one of the focal spot shifting technique and the quarter-detector shifting technique is applied) while maintaining high image quality.

Returning to FIG. 1, when channels comprise a detection portion 1004 and a dead space 1006, the correction component 124 (e.g., which may comprise one or more microprocessors), may be configured to correct for the dead space 1006 within the respective channels based upon information acquired from the detection portions of the channels. For example, the correction component 124 may be configured to take into account quarter-detector shift and/or flying focal spot information in order to improve the projection sampling frequency, and also to perform additional interpolation functions, for example, in order to compensate for dead spaces. That is, the correction component 124 may correct for the difference between the actual size of the detector array (e.g., as measured based upon the detection portions of respective channels) and the effective size (which is measured as the total area, including the area(s) of the dead space).

Figure 14:
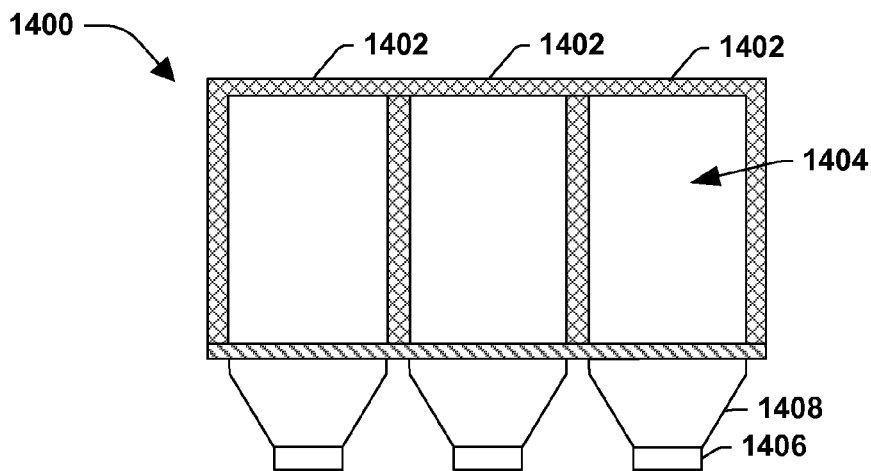
FIG. 14 illustrates a cross-sectional view of example channels of an indirect conversion detector array, respective channels comprising a light focusing mechanism configured to focus light from a scintillator material to an underlying photodetector.

FIG. 14 illustrates yet another environment (e.g., cross-section view) of a detector array having an effective area that is greater than its actual area. Specifically, FIG. 14 illustrates three channels 1402 of an indirect conversion detector array (e.g., similar to that described with respect to FIG. 2). The channels respectively comprise a scintillator material 1404 (e.g., such as Cadmium Tungstate, Zinc Tungstate, Cesium Iodide etc.), a photodetector 1406, and a microlense 1408. It will be appreciated that the example channels 1402 of an indirect detector array merely illustrate one embodiment and other possible configurations are contemplated herein.

As illustrated, between the scintillator material 1404 and the photodetector 1406 resides a light focusing mechanism 1408 (e.g., such as microlense or other component having properties suited for focusing light) configured to focus light generated by a larger area (e.g., as measured from the perspective of the radiation source) of the scintillator material 1404 onto a photodetector 1406 having a smaller area. Stated differently, between the scintillator material and the photodetector resides a mechanism 1408 that is configured to funnel the light. Thus, the area of the detection surface of the scintillator 1404 is larger than the area of the detection surface of the photodetector 1406 (e.g., providing for cost savings by requiring less/fewer materials in photodetector 1406).

It will be appreciated that in such an embodiment, the actual area (e.g., the area of the detection surface) of the scintillator material 1404 may be substantially equal to the effective size of the detector array. However, the actual area (e.g., the area of the detection surface) of the photodetector 1406 may be less than the effective size of the detector array.

Moreover, it will be appreciated that in such an embodiment, no correction may have to be performed on the information acquired from the detector because substantially all of the emitted radiation is being detected and/or measured. The difference being that the light yielded from the scintillator material 1404 is focused onto a smaller area of the photodetector 1406, allowing the photodetector 1406 to be reduced in size (e.g., relative to the prior art photodetector 208 in FIG. 2).

It will also be appreciated to those skilled in the art that while reference is made herein to three different configurations of detector arrays (e.g., sparse arrays, arrays comprising channels that respective have a detection portion and a dead space, and arrays comprising light focusing mechanisms), one or more of the configurations may be combined together to form a detector array having an effective size that is greater than its actual size. For example, in a direct conversion detector array, a sparse array configuration (e.g., as illustrated in FIGS. 4-8) can be combined with channels comprising detection portions and dead space (e.g., as illustrated in FIG. 10) to further reduce the actual size of the detector array (e.g., while keeping the effective size substantially constant), relative to the possible actual size if merely one of the disclosed techniques were implemented.

In an indirect conversion detector array, for example, all three configurations can be combined into a single detector array to substantially reduce the actual area of the detector array (e.g., while maintaining an effective area substantially equal to the actual area of the prior art detector array). In another embodiment, the sparse array configuration (e.g., as illustrated in FIGS. 4-8) is merely combined with a configuration where channels are comprised of a detection portion and dead space (e.g., as illustrated in FIG. 10). In another embodiment, the sparse array configuration (e.g., as illustrated in FIGS. 4-8) is merely combined with the light focusing configuration (e.g., as illustrated in FIG. 14). In yet another embodiment, the configuration where the channels are comprised of a detection portion and dead space (e.g., as illustrated in FIG. 10) may be combined with the light focusing configuration (e.g., as illustrated in FIG. 14). Thus, a plurality of configurations of the detector array are possible to make the actual size of the detector array (e.g., as measured by the total detection surface area) less than its effective size.

It will be appreciated that there are numerous benefits to making the actual size of the detector array smaller than its effective size. For example, in doing so, the amount of detector material (e.g., direct conversion detector material, scintillator material, and/or photodetectors) may be reduced, causing the cost of the detector array to be reduced. This, in turn, may decrease the total cost of the radiation scanner, allowing such scanners to be cost effective in areas where the cost presently makes their implementation difficult (e.g., such as in certain industrial applications), economically troubled countries, etc.

Figure 15:
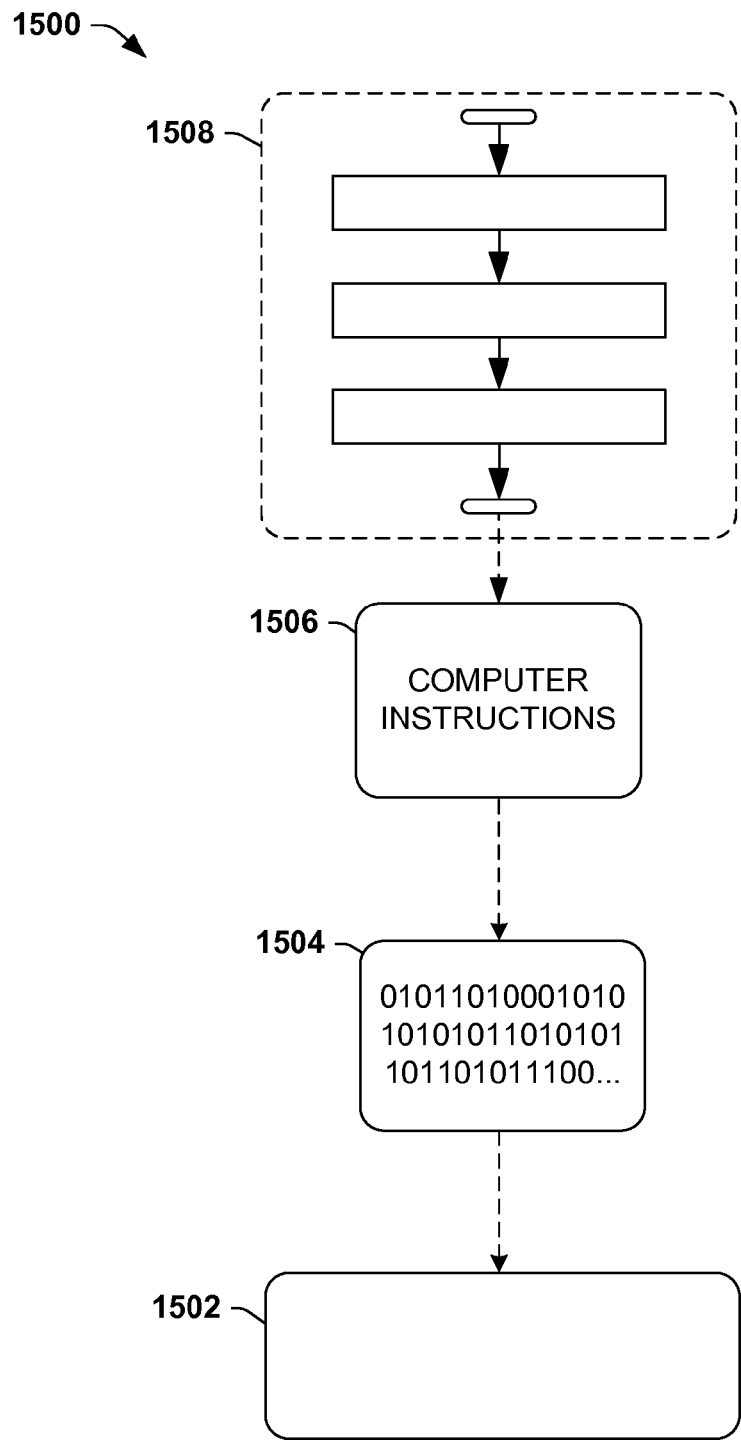
FIG. 15 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 15, wherein the implementation 1500 comprises a computer-readable medium 1502 (e.g., a CD-R, DVD-R, platter of a hard disk drives, flash/thumb drive, etc.), on which is encoded computer-readable data 1504. This computer-readable data 1504 in turn comprises a set of computer instructions 1506 configured to operate according to one or more of the principles set forth herein. In one such embodiment 1500, the processor-executable instructions 1506 may be configured to perform a method 1508, such as at least some of the example method 900 of FIG. 9, for example. Many such computer-readable media may be devised by those of ordinary skill in the art that are configured to operate in accordance with one or more of the techniques presented herein.

It will be appreciated that the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A radiation examination apparatus comprising:
   a detector array comprising a first set of channels defining a first portion of a detection surface and a second set of dead spaces defining a second portion of the detection surface, wherein a dead space of the second set is disposed between a first channel of the first set and a second channel of the first set and a pitch between the first channel and the second channel is at least two times a width of the first channel; and
   a correction component configured to perform interpolation using information acquired from one or more channels of the first set neighboring the dead space to approximate an amount of radiation impingent upon the dead space such that the detector array has an effective size that is greater than an actual size of a portion of the detection surface defined by the first set of channels.

2. The radiation examination apparatus of claim 1, wherein the first set of channels and the second set of dead spaces are arranged in a pattern.

3. The radiation examination apparatus of claim 1, wherein the first set of channels and the second set of dead spaces are arranged in a checkerboard pattern.

4. The radiation examination apparatus of claim 1, wherein the first set of channels are arranged in a grid pattern and the dead space is situated between at least one of:
   two adjacent rows of channels, or
   two adjacent columns of channels.

5. The radiation examination apparatus of claim 1, wherein the first set of channels are arranged in a grid pattern and wherein:
   the dead space is situated between two adjacent rows of channels and between two adjacent columns of channels.

6. The radiation examination apparatus of claim 1, wherein the dead space has a width substantially equal to the width of the first channel and a depth substantially equal to a depth of the first channel.

7. The radiation examination apparatus of claim 1, the first set of channels and the second set of dead spaces arranged in a grid pattern comprising columns and rows, wherein:
   the dead space is situated in a row between the first channel and the second channel, and
   the dead space is situated in a column between a third channel and a fourth channel of the first set.

8. The radiation examination apparatus of claim 1, comprising a radiation source configured to emit radiation from at least two locations via a flying focal spot.

9. The radiation examination apparatus of claim 8, the information indicative of radiation emitted while the radiation source was at a first location of the at least two locations and radiation emitted while the radiation source was at a second location of the at least two locations.

10. The radiation examination apparatus of claim 1, wherein the information is indicative of radiation detected during a single view of an object under examination.

11. The radiation examination apparatus of claim 1, wherein the detector array is shifted relative to a center beam of radiation such that a center channel of the first set of channels is not aligned with the center beam of radiation.

12. The radiation examination apparatus of claim 1, the information comprising first information yield from radiation detected while the detector array was at a first location relative to an object under examination and second information yielded from radiation detected while the detector array was at a second location relative to the object under examination, the second location substantially 180 degrees apart the first location.

13. The radiation examination apparatus of claim 1, wherein the detector array is an indirect conversion detector array and channels of the first set respectively comprise at least a scintillator material and a photodetector.

14. The radiation examination apparatus of claim 13, wherein the channels respectively comprise a light focusing mechanism, the light focusing mechanism situated between the scintillator material and the photodetector.

15. The radiation examination apparatus of claim 14, wherein the light focusing mechanism comprises a microlens.

16. The radiation examination apparatus of claim 13, wherein a detection surface of the scintillator material has a first area and a detection surface of the photodetector has a second area, the first area larger than the second area.

17. A radiation examination apparatus, comprising:
   a detector array comprising a first set of channels and a second set of dead spaces, the first set of channels and the second set of dead spaces arranged in a grid pattern wherein a first row of dead spaces are situated between a first row of channels and a second row of channels and wherein a pitch between the first row of channels and the second row of channels is at least two times a width of the first row of channels.

18. The radiation examination apparatus claim 17, comprising a correction component configured to perform interpolation using information acquired from one or more channels of the first set neighboring a dead space of the second set to approximate an amount of radiation impingent upon the dead space.

19. The radiation examination apparatus of claim 17, wherein the detector array is a direct conversion detector array configured to convert radiation directly into electric charge.

20. The radiation examination apparatus of claim 17, wherein the detector array is an indirect conversion detector array and the first set of channels respectively comprise a scintillator material configured to convert radiation into light and a photodetector configured to convert the light into electric charge.

21. The radiation examination apparatus of claim 20, wherein respective channels comprise a light focusing mechanism positioned between the scintillator material and the photodetector.

22. A method, comprising:
performing interpolation using information acquired from one or more channels neighboring a dead space to approximate an amount of radiation impingent upon the dead space to correct for a difference between an actual area of a portion of a detection surface comprising the one or more channels of a detector array and an effective area of the detection surface of the detector array, the dead space disposed between a first channel and a second channel and a pitch between the first channel and the second channel at least two times a width of the first channel.

23. The method of claim 22, comprising:
acquiring the information from the first channel disposed in a first row of the detector array and the second channel disposed in a second row of the detector array, the dead space situated in a third row of the detector array, the third row between the first row and the second row.

24. The method of claim 23, wherein a z-dimension of the third row is substantially equal to a z-dimension of at least one of the first row or the second row.

25. The method of claim 22, the acquiring comprising:
acquiring the information from a third channel of the one or more channels disposed in a first column of the detector array and a fourth channel of the one or more channels disposed in a second column of the detector array, the dead space situated in a third column of the detector array, the third column between the first column and the second column.

* * * * *